United States Patent
Kotera et al.

(10) Patent No.: US 8,003,062 B2
(45) Date of Patent: Aug. 23, 2011

(54) MICROCHANNEL FOR SEPARATING BLOOD PLASMA

(75) Inventors: Hidetoshi Kotera, Kyoto (JP); Masao Washizu, Tokyo (JP); Hidehiro Oana, Tokyo (JP)

(73) Assignee: Kyoto University, Kyoto-Shi, Kyoto (JP)

( * ) Notice: Subject to any disclaimer, the term of this patent is extended or adjusted under 35 U.S.C. 154(b) by 212 days.

(21) Appl. No.: 12/227,400

(22) PCT Filed: May 22, 2007

(86) PCT No.: PCT/JP2007/060430
§ 371 (c)(1),
(2), (4) Date: Nov. 21, 2008

(87) PCT Pub. No.: WO2007/136057
PCT Pub. Date: Nov. 29, 2007

(65) Prior Publication Data
US 2009/0107909 A1    Apr. 30, 2009

(30) Foreign Application Priority Data
May 24, 2006  (JP) ................................ 2006-143886

(51) Int. Cl.
*B01D 17/025*    (2006.01)
(52) U.S. Cl. ........ 422/503; 422/504; 137/807; 137/814; 137/825; 210/320; 210/513; 210/532.1
(58) Field of Classification Search .......................... None
See application file for complete search history.

(56) References Cited

U.S. PATENT DOCUMENTS

| | | | | |
|---|---|---|---|---|
| 4,409,106 A * | 10/1983 | Furuta et al. | ................... | 210/732 |
| 4,424,132 A * | 1/1984 | Iriguchi | ........................ | 210/800 |
| 2004/0053422 A1 * | 3/2004 | Chan et al. | ..................... | 436/180 |
| 2004/0069717 A1 * | 4/2004 | Laurell et al. | .................. | 210/748 |
| 2006/0033243 A1 * | 2/2006 | Sundararajan | ................ | 264/494 |
| 2006/0228263 A1 * | 10/2006 | Berndtsson et al. | .......... | 422/100 |
| 2006/0275184 A1 * | 12/2006 | Furukawa et al. | ............. | 422/129 |
| 2008/0073297 A1 * | 3/2008 | Shiraishi et al. | .............. | 210/800 |

FOREIGN PATENT DOCUMENTS

| | | |
|---|---|---|
| JP | S57-131451 | 8/1982 |
| JP | S58-041822 | 3/1983 |
| JP | 2004-109082 | 4/2004 |
| JP | 2005-300528 | 10/2005 |
| JP | 2006-017562 | 1/2006 |
| JP | 2006-058093 | 3/2006 |
| JP | 2006-058280 | 3/2006 |

* cited by examiner

*Primary Examiner* — In Suk Bullock
*Assistant Examiner* — Timothy G Kingan
(74) *Attorney, Agent, or Firm* — Manabu Kanesaka (57) ABSTRACT

A microchannel has a substrate body; a separation channel which is formed within the substrate; at least two (first and second) connection ports which are formed at one end of the separation channel close to the thickness direction perpendicular to the longitudinal direction of the substrate body; and first and second branch channels connected respectively to the first and second connection ports. When the substrate body is perpendicular to gravity, a blood sample containing blood cells and plasma, flows from one end of the separation channel. Before the blood sample gets to the other end of the separation channel, the blood cells in the blood sample settle out. The blood cells having settled out are then separated into the branch channel.

10 Claims, 9 Drawing Sheets

MICROCHANNEL FOR SEPARATING BLOOD PLASMA

TECHNICAL FIELD

The present invention relates to a microchannel for separating blood plasma, and particularly relates to a channel structure for separating blood cells and blood plasma in a blood sample on a microchip etc., for blood examinations.

BACKGROUND ART

Blood examinations are the most common procedure for medical checkups. In recent years, technological developments for performing blood examinations on microchips have been advanced. Thus, by using such an on-chip system, there have been expectations in reducing pain from blood sampling with a decrease in the required blood amount, downsizing apparatuses, speeding up examinations through point-of-care testing and reducing examination costs by decreasing reagent amounts, etc.

Meanwhile, most examination items in blood examinations are associated with soluble components in blood, and the blood cells which occupy approximately 50% volume in the blood are components which hinder these examinations. Thus, prior to an examination, it is required to acquire only blood plasma by separating blood plasma from the blood cells.

In conventional methods, a method of using a filter, a method of precipitating the blood cells by a centrifuge and a method of coagulating the blood cells by adding an agent, and the like have been adopted for this blood plasma separation. It is conceivable that these methods are also applied when a blood examination is performed on the microchip.

For example, in Patent Document 1, an analysis chip for separating blood cells using a porous body for a pretreatment element has been disclosed.

Also in Patent Documents 2 and 3, it has been proposed that blood components are separated by a gravitational force in a process where the blood is continuously flown. For example, in an apheresis system having a sealed container 101 shown by a partial cross section perspective view in FIG. 12, the blood to which an anticoagulant has been added is passed through an introduction path 103 and introduced from a blood introduction inlet 103a to one of the blood channels 102 continuously. As the blood is flown along the blood channel 102, the blood is separated into a supernatant layer 104 composed of blood plasma containing rich platelets and a precipitation layer 105 composed of the blood cells such as erythrocytes and leukocytes. And, at an end of a downstream of the blood channel 102, the blood plasma containing the rich platelets in the supernatant layer 104 is discharged from a discharge path 106 by passing through a discharge outlet 106a provided at the shallowest site. The blood cells in the precipitation layer 105 are discharged from a discharge path 107 by passing through a discharge outlet 107a provided at the deepest site. For example, the volume of the blood channel 102 is approximately 300 mL, and the blood introduced at a flow volume of approximately 20 mL/minute is separated in a residence time of approximately 15 minutes in the sealed container 101.

Patent Document 1: Japanese Published Unexamined Patent Application No. 2006-58280
Patent Document 2: Japanese Published Unexamined Patent Application No. S57-131451
Patent Document 3: Japanese Published Unexamined Patent Application No. S58-41822

DISCLOSURE OF THE INVENTION

Problems to be Solved by the Invention

However, the method of using the filter has shortcomings that hemolysis easily occurs and the blood plasma absorbed in the filter becomes useless. The method by the centrifuge has shortcomings that the apparatus itself is large and is not always compatible with the microchip etc. The method of using a coagulant has shortcomings that the coagulant itself can become a hindering component in the examination and is likely to occlude the microchannel etc.

Figure 12:
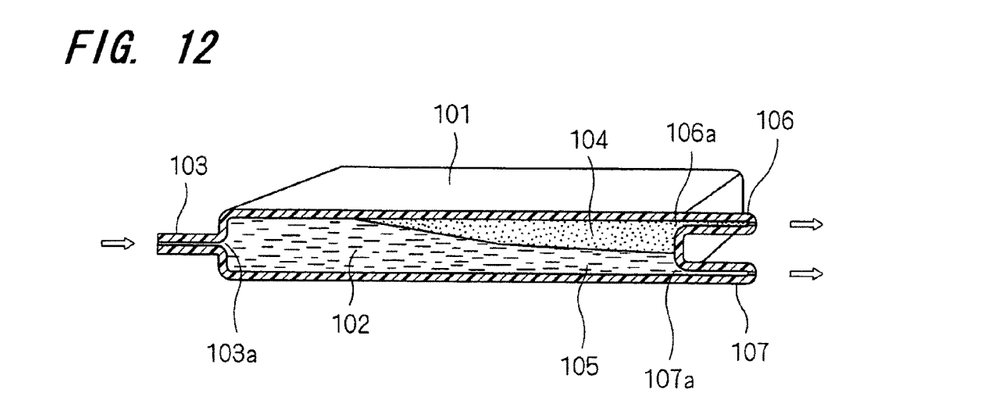
FIG. 12 is a partial cross sectional perspective view of an apheresis system of blood (prior art).

Also in the apheresis system shown in FIG. 12, it is constructed so that the end of the downstream of the blood channel 102 is provided with the discharge outlets 106a and 107a separated up and down, and the cross section of the channel is rapidly changed. Accordingly, it is necessary that flow volumes of the supplied and discharged blood are controlled and the components of blood are slowly separated taking time so that a state where the blood components are separated downstream of the blood channel 102 is not disrupted. The flow rate in the blood channel 102 is slower than those in the discharge paths 106 and 107. Even if such a constitution is directly downsized, it is difficult to efficiently separate the blood in a very small amount.

In consideration of such actual circumstances, the present invention provides a microchannel for separating blood plasma whereby blood plasma can be conveniently separated on a microchip.

Means for Solving the Problems

The present invention provides a microchannel for separating blood plasma constituted as follows, in order to solve the above problems.

The microchannel for separating blood plasma includes (a) a substrate body, (b) a separation channel which is formed inside the substrate body and extended in parallel to a longitudinal direction of the substrate body, and (c) at least two, first and second communication ports which are formed at one end of the separation channel closely to a thickness direction perpendicular to the longitudinal direction of the substrate body, and (d) first and second branch channels which are formed inside the substrate body and communicated with the first and second communication ports, respectively. In the state where the substrate body is extended perpendicularly in a direction of gravitational force, a blood sample containing blood cells and blood plasma is flown from the other end of the separation channel, and the blood cells in the blood sample settle out before the blood sample reaches the one end of the separation channel. The blood cells having settled out are introduced into one located at a lower side of the direction of gravitational force among the first and second branch channels, and a majority of the blood plasma is introduced into the other one located at a higher side of the direction of gravitational force in the first and second branch channels.

In the above constitution, the blood cells settle out when the blood sample is flown in the separation channel, and in the downstream side, the blood cells are flown in an under side of the separation channel. And, as the state where the blood cells are flown in the lower side of the separation channel is kept, the blood sample is introduced from the first and second communication ports formed closely up and down to the first and second branch channels to make a branch, and the blood cells are flown in the lower branch channel and the supernatant other than the blood cells is flown in the upper branch channel. Thereby, the supernatant containing no blood cells, i.e., the blood plasma can be acquired from the upper branch channel.

According to the above constitution, by forming the first and second communication ports closely, it is possible to introduce the blood sample separating its components with flowing in the separation channel to the first and second communication ports in one end of the separation channel without disrupting a separation state of the blood components (particularly a border interface of the blood components) and branch the components there and make the flow rate before and after the branching substantially constant. Thus, it is possible to efficiently separate the blood sample even in a very small amount.

Preferably, a separator structure which projects from one end to the other end in the separation channel and divides the one end of the separation channel into at least two portions in the thickness direction is further included. The portions divided by the separator structure are communicated with the first and second communication ports, respectively.

In this case, by the separator structure, in the separation channel it is possible to separate the blood flow state up and down without disrupting a laminar flow where the blood cells are flown in the lower side of the separation channel and enhance the accuracy of the blood plasma separation.

Preferably, the substrate body includes first and second substrates which are mutually joined. A portion of one side in the thickness direction of the separation channel is formed on the first substrate, and a portion of the other side in the thickness direction of the separation channel is formed on the second substrate. The separator structure is constituted by a sheet-like member held between the first and second substrates so as to traverse the one end side of the separation channel.

In this case, by sandwiching the sheet-like member between the substrates, it is possible to simply form the separator structure.

More preferably, first and second columnar structures extending in the thickness direction are formed respectively in the one end sides of the first and second portions of the separation channel formed on the first and second substrates. The sheet-like member which composes the separator structure is held between the first columnar structure and the second columnar structure.

In this case, the sheet-like member which composes the separator structure is held between the first columnar structure in the side of the first substrate and the second columnar structure in the side of the second substrate, and is supported mechanically. Thus, it is possible to prevent a deformation due to a surface tension when the blood sample enters the separator structure (sheet-like member).

Preferably, an inner surface of the separation channel has the contact angle of 70 degrees or more with respect to the blood sample.

In this case, the blood sample forms a uniform flow upon separating the blood cells in the separation channel. Thus, the accuracy of the blood plasma separation can be enhanced.

Preferably, a depth in a normal line direction in the separation channel is 1 mm or less.

In this case, it is possible to settle out the blood cells in a short period of time, keep the laminar flow state by reducing the Reynolds number and separate the blood plasma from the blood sample in a very small amount.

Also, the present invention provides a microchannel for separating blood plasma constituted as follows in order to solve the above problems.

The microchannel for separating the blood plasma includes (a) the substrate body containing a first substrate having first and second planes which are mutually parallel and a second substrate having third and fourth planes which are mutually parallel, where the second plane in the first substrate and the third plane in the second substrate are joined, (b) a main channel formed by disposing a first groove formed on the second plane in the first substrate and a second groove formed on the third plane in the second substrate to be mutually facing and extending along an interface between the second plane in the first substrate and the third plane in the second substrate, (c) first and second communication ports formed respectively in the first groove in the first substrate and the second groove in the second substrate in one end side of the main channel and (d) first and second branch channels formed respectively on the second plane in the first substrate and on the third plane in the second substrate by communicating with the first communication port and the second communication port and extending along the interface to be mutually separate. The main channel has a structure where a blood sample including the blood cells and the blood plasma is flown as the laminar flow state from the other end to the one end in the main channel in the state where the interface is disposed to extend perpendicularly to the direction of gravitational force. The blood cells in the blood sample settle out in the lower side of the direction of gravitational force before the blood sample reaches the one end of the main channel. The blood cells are introduced into one located at the lower side of the direction of gravitational force in the first and second branch channels, and the majority of the blood plasma is introduced into the other one located at the higher side of the direction of gravitational force in the first and second branch channels.

Preferably, the microchannel for separating the blood plasma further includes a separator structure which projects from the one end to the other end in the main channel and divides the one end of the main channel into at least two portions in the direction perpendicular to the interface. The portions divided by the separator structure are communicated with the first and second communication ports, respectively.

Preferably, the separator structure is constituted by a sheet-like member held between the first and second substrates so as to traverse the one end side of the main channel.

Preferably, first and second columnar structures which extend in the direction perpendicular to the interface are formed respectively in the one end sides of the first and second grooves of the main channel formed on the first and second substrates. The sheet-like member which composes the separator structure is held between the first structure and the second columnar structure.

Preferably, the inner surface of the main channel has a contact angle of 70 degrees or more with respect to the blood sample.

Preferably, the depth of the main channel is 1 mm or less in the direction perpendicular to the interface.

EFFECT OF THE INVENTION

According to the present invention, the blood plasma can be separated conveniently on the microchip by utilizing the settling-out of the blood cells in the microchannel, keeping the laminar flow state in the channel and acquiring the supernatant including the blood plasma by the branch channel.

DESCRIPTION OF SYMBOLS

10: Microchip for blood examination (microchannel for separating blood plasma)
10a: Substrate body
11: Separation channel (main channel)
13, 14: Branch channel (first and second branch channels)
13a, 14a: Communication port (first and second communication ports)
16: Separator structure
20: Lower substrate (first substrate)
28: Columnar structure (first columnar structure)
30: Upper substrate (second substrate)
38: Columnar structure (second columnar structure)
40: Thin plate (sheet-like member)
100: Microchip for blood examination (microchannel for separating blood plasma)
110: Separation channel (main channel)
113, 114: Branch channel
120: Lower substrate (first substrate)
130: Upper substrate (second substrate)
140: Thin plate (sheet-like member)
200: Microchip array for blood examination (microchannel for separating blood plasma)
210: Substrate body
212: Substrate (first substrate)
214: Substrate (second substrate)
230: Main channel (Separation channel)
232, 234: Branch channel

BEST MODES FOR CARRYING OUT THE INVENTION

Embodiments of the present invention will be described below with reference to FIG. 1 to FIG. 11.

Embodiment 1

The microchip for blood examinations (herein after also referred to as the "microchip" simply) according to Embodiment 1 of the present invention will be described using FIG. 1 to FIG. 4.

A basic constitution of the microchip 10 is described with reference to FIG. 1. FIG. 1(a) is a plane transparent view and FIG. 1(b) is a cross sectional view cut along a line b-b in FIG. 1(a).

Figure 1:
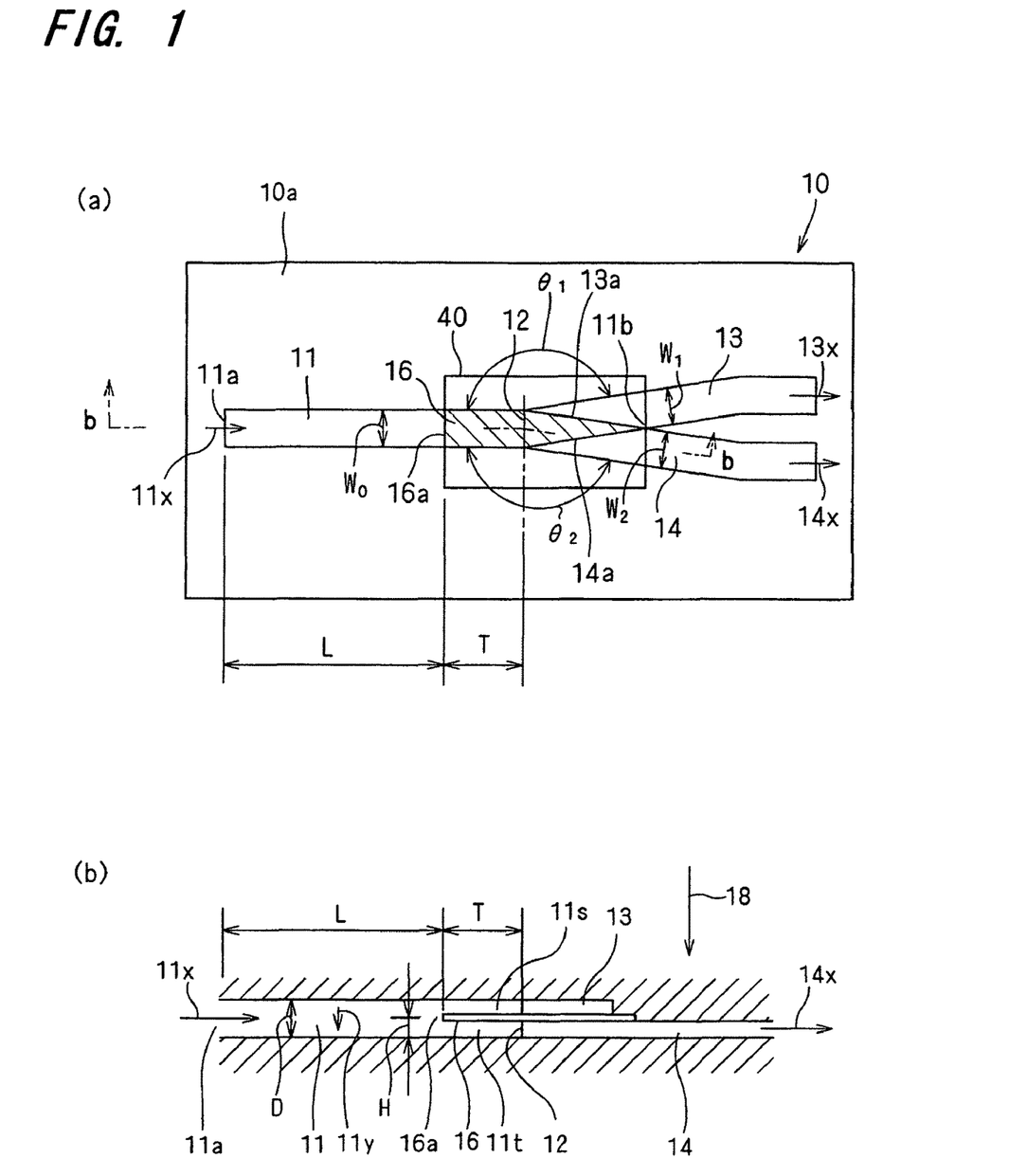
FIG. 1 is (a) a plane transparent view and (b) a cross sectional view of a microchip for blood examinations (Embodiment 1)

As shown in FIG. 1(a), in the microchip 10, the channels 11, 13, 14 in a nearly Y-shape which are substantially parallel to a longitudinal direction of a substrate body 10a are formed inside the substrate body 10a which is a main body of the microchip 10. That is, a first branch channel 13 and a second branch channel 14 are branched from communication ports 13a, 14a formed closely to a thickness direction perpendicular to the longitudinal direction of the substrate body 10a in one end 11b side in the separation channel 11.

A blood sample is supplied from the other end 11a side to the separation channel 11. The blood sample settles out the blood cells when flowing in the separation channel 11, and in a downstream side, the blood cells are flown in a lower side of the separation channel 11. And, as the blood sample keeps the state where the blood cells are flown in the lower side of the separation channel 11, the blood sample is introduced from the communication ports 13a, 14a formed closely up and down the branch channels 13, 14, and branched there. At this time, by flowing the blood cells in the lower branch channel 14 and flowing the supernatant other than the blood cells in the upper branch channel 13, it is possible to acquire the supernatant containing no blood cells, i.e., the blood plasma from the upper branch channel 13.

Since the communication ports 13a, 14a are formed closely, the blood sample which is flown in the separation channel 11 and has separated blood components can be introduced into the communication ports 13a, 14b in the one end 11b side of the separation channel 11 without disrupting the separation state of the blood components (particularly, an interface of the blood components). The blood sample can be flown from the separation channel 11 to the branch channels 13, 14 at a nearly constant flow rate. Therefore, a blood sample even in a very small amount can be separated efficiently.

If a separator structure 16 (portion of pentagon with slant lines) which divides the separation channel 11 up and down is provided near the one end 11b in the separation channel 11, the blood components can be more efficiently separated. The separator structure 16 is composed of the portion disposed in the separation channel 11 in a thin plate 40 which traverses near the one end 11b of the separation channel 11. The separator structure 16 is extended from a position (branch starting position) 12 where the branch channels 13, 14 start to branch from the separation channel 11 to the other end 11a side of the separation channel 11. It is preferable that a distance T between a tip 16a of the separator structure 16 and the branch starting position 12 is T≧0 so that the flow is not disrupted upon being branched.

As shown in FIG. 1(b), the separator structure 16 is extended in parallel to the longitudinal direction of the separation channel 11, and divides the separation channel 11 into two parts 11s and 11t. The first branch channel 13 and the second branch channel 14 are communicated with the parts 11s and 11t divided by this separator structure 16, respectively.

The substrate body 10a is substantially horizontally disposed, respective channels 11, 13, 14 are disposed to extend in the direction substantially perpendicular to the direction of gravitational force shown by an arrow 18, i.e., in a substantially horizontal direction, and the blood sample is supplied from the other end 11a in the separation channel 11, as shown by the arrow 11x. When the blood sample is flown in the separation channel 11, the blood cells in the blood sample settle out by the gravitational force as shown by the arrow 11y, and the blood cells are flown in the lower side of the direction of gravitational force in the more downstream portion (one end 11b side of the separation channel 11) of the separation channel 11. Meanwhile, the blood plasma in the blood sample is flown in the side opposite to that of the blood cells, i.e., in the upper side of the direction of gravitational force in the more downstream portion of the separation channel 11.

By appropriately setting the flow rate v when the blood sample flows in the separation channel 11 and the distance L where the blood sample flows until reaching the tip 16a of the separator structure 16, it is possible to separate the blood cells to the lower side of the direction of gravitational force and the blood plasma to the upper side of the direction of gravitational force when the blood sample reaches the tip 16a of the separator structure 16.

That is, standard values for an erythrocyte sedimentation rate in clinical laboratory tests are within 10 mm in males and within 15 mm in females for one hour. Thus, a sedimentation velocity $v_s$ of the blood cell is approximately 3 to 4 μm/second under the usual gravitational force. When a length of the separation channel 11 from the other end 11a of the separation channel 11 to the tip 16a of the separator structure 16 is L, the depth of the separation channel 11 is D, the flow rate of the blood sample is v and the sedimentation velocity of the blood cells in the blood sample is $v_s$, if the parameters are set to satisfy $$L > (v/v_s) \times d \quad (1),$$

the blood cells are separated to the lower side of the direction of gravitational force and the blood plasma is separated to the upper side of the direction of gravitational force when the blood sample reaches the tip 16a of the separator structure 16.

If a height H of the separator structure 16 is made nearly equivalent to the height of the blood cells settling out when the blood sample reaches the tip 16a of the separator structure 16, all or the majority of the blood cells flow into the part 11t which is the lower side of the direction of gravitational force of the separator structure 16, and the majority of the blood plasma flows into the part 11s which is the higher side of the direction of gravitational force of the separator structure 16. Thereby, it is possible to introduce the blood plasma to the first branch channel 13 and introduce the blood cells to the second branch channel 14.

The separator structure 16 in FIG. 1 has a thin platy structure, but is not limited thereto, and may have any structure such as the structure having an edge-like cusp as long as the structure can divide the flow into two in the direction of gravitational force.

If the channels 11, 13 and 14 are constituted to have a uniform cross section and extend in the horizontal direction, the flow is hardly disrupted, which is preferable, but their constitution is not limited thereto. For example, the cross section of the channels 11, 13 and 14 may be changed. The separation channel 11 may be extended in a non-horizontal direction as long as the blood cells can settle out by utilizing the gravitational force. The channels 13 and 14 may also be extended in the non-horizontal direction.

As shown in FIG. 1(a), if angles $\theta_1$ and $\theta_2$ of the first and second branch channels 13 and 14 branching against the separation channel 11 are close to 180°, this is preferable because the flow is scarcely disrupted, but the angles may have any value.

Figure 2:
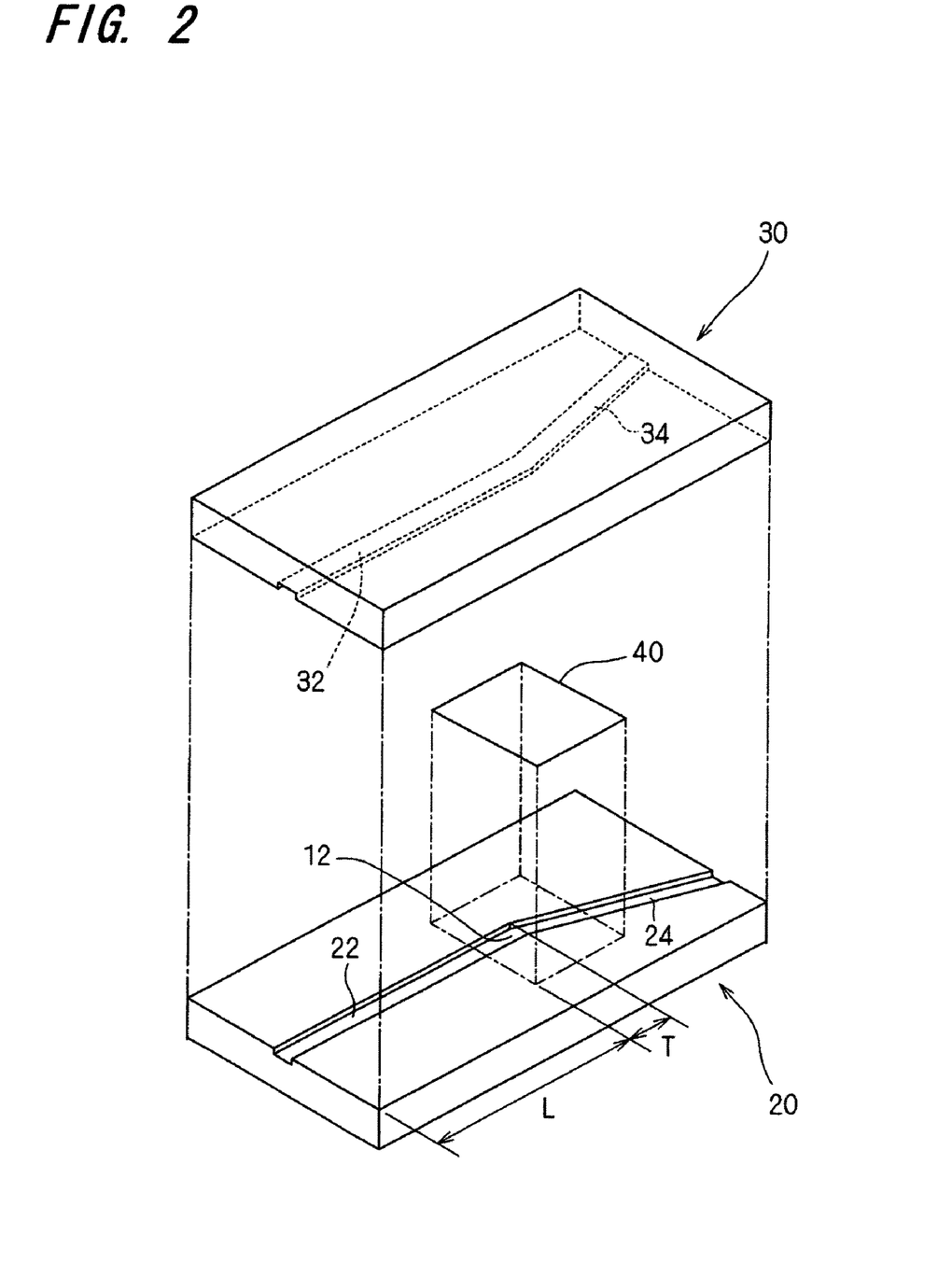
FIG. 2 is an exploded perspective view of the microchip for blood examinations (Embodiment 1)

As shown in the explored perspective view in FIG. 2, the microchip 10 can be produced by pasting two substrates 20 and 30 having grooves 22 and 24; 32 and 34 formed on its one principal surface so as to sandwich a thin plate 40 between them. The grooves 22 and 32 which become parts of the separation channel 11, the groove 24 which becomes the second branch channel 14 and the groove 34 which becomes the first branch channel 13 are previously formed respectively on the substrates 20 and 30 by injection or embossing. And, the substrates 20 and 30 are pasted together by fitting positions of the grooves 22 and 32 whose parts become the separation channel 11 so as to sandwich the thin plate between them.

The method for producing the microchip is not limited thereto. For example, the channels 11, 13 and 14 and the separator structure 16 may be formed inside the substrate body 10a using a photocurable resin.

Figure 3:
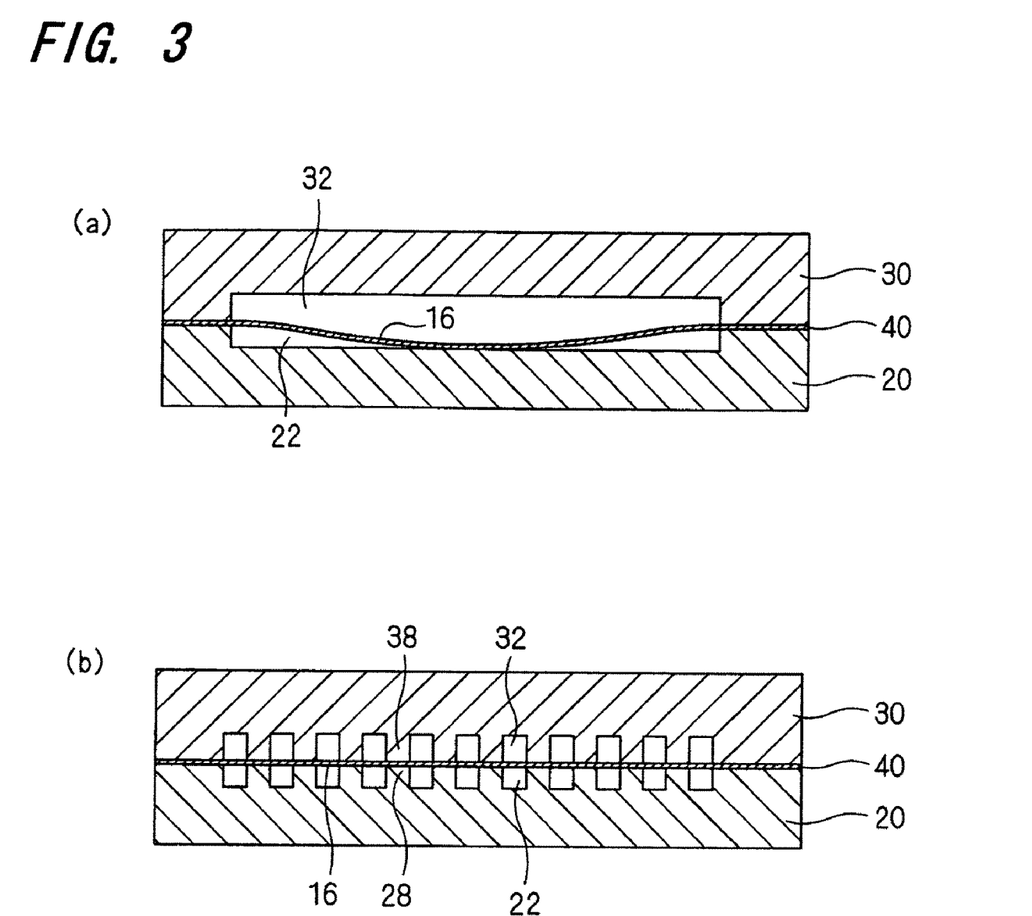
FIG. 3 is cross sectional views of a channel bifurcation (Embodiment 1)

When the separator structure 16 is composed of the thin plate 40, depending on the thickness and the material etc., of the thin plate 40, the thin plate 40 is pulled due to a surface tension when the blood sample enters the separator structure 16, and the separator structure 16 is deformed in some cases, for example, as shown in FIG. 3(a).

In order to prevent this, as shown in FIG. 3(b), the separator structure 16 may be supported mechanically by making columnar structures 28 and 38 in the grooves 22 and 32 in the substrates 20 and 30 which become the separation channel 11 (see FIG. 1) to sandwich the thin plate 40 between the columnar structures 28 and 38.

The columnar structures 28 and 38 may also be provided in the branch channels 13 and 14 to press the thin plate 40 exposed to the branch channels 13 and 14 to channel wall surfaces.

The period of time required for the separation of the blood plasma using the microchip 10 is determined by the period of time required for the settling-out of blood, and is proportional to the depth of the separation channel 11. In general, it is desirable that blood examinations on the chip is terminated in approximately several minutes. Thus, it is preferable that the depth D (see FIG. 1(b)) of the separation channel 11 does not exceed 1 mm.

The condition to successfully separate the blood plasma using the microchip 10 consists in keeping the flow in the laminar flow state in the separation channel 11. If this state is collapsed, the settling-out of the blood cells is disrupted or the separated blood plasma and blood cells are mixed again. Therefore, also for keeping the laminar flow state by reducing the Reynolds number, it is required that the depth D of the separation channel 11 is 1 mm or less.

In general, if the channel is hydrophilic, a water soluble fluid is spontaneously drawn into the channel due to a capillary phenomenon. At this time, if the hydrophilicity is too strong, the capillary phenomenon acts strongly upon a corner portion of the channel cross section. Thus, the fluid is first drawn in along this corner portion and does not uniformly flow in the cross section inside the channel. Thus, the laminar flow state is disrupted. In order to uniformly flow in the separation channel 11 to settle out the blood cells, it is necessary that a channel wall surface of the separation channel 11 is comparatively hydrophobic, e.g., the contact angle with respect to the blood is 70 degrees or more. Thus, to use glass as the material for the substrates 20 and 30 which form the separation channel 11, coating of a channel inner wall with an organic material such as parylene or silane coupler is required.

<Example of production> Subsequently, an example of producing the microchip will be described.

(1) Production of Template

Figure 4:
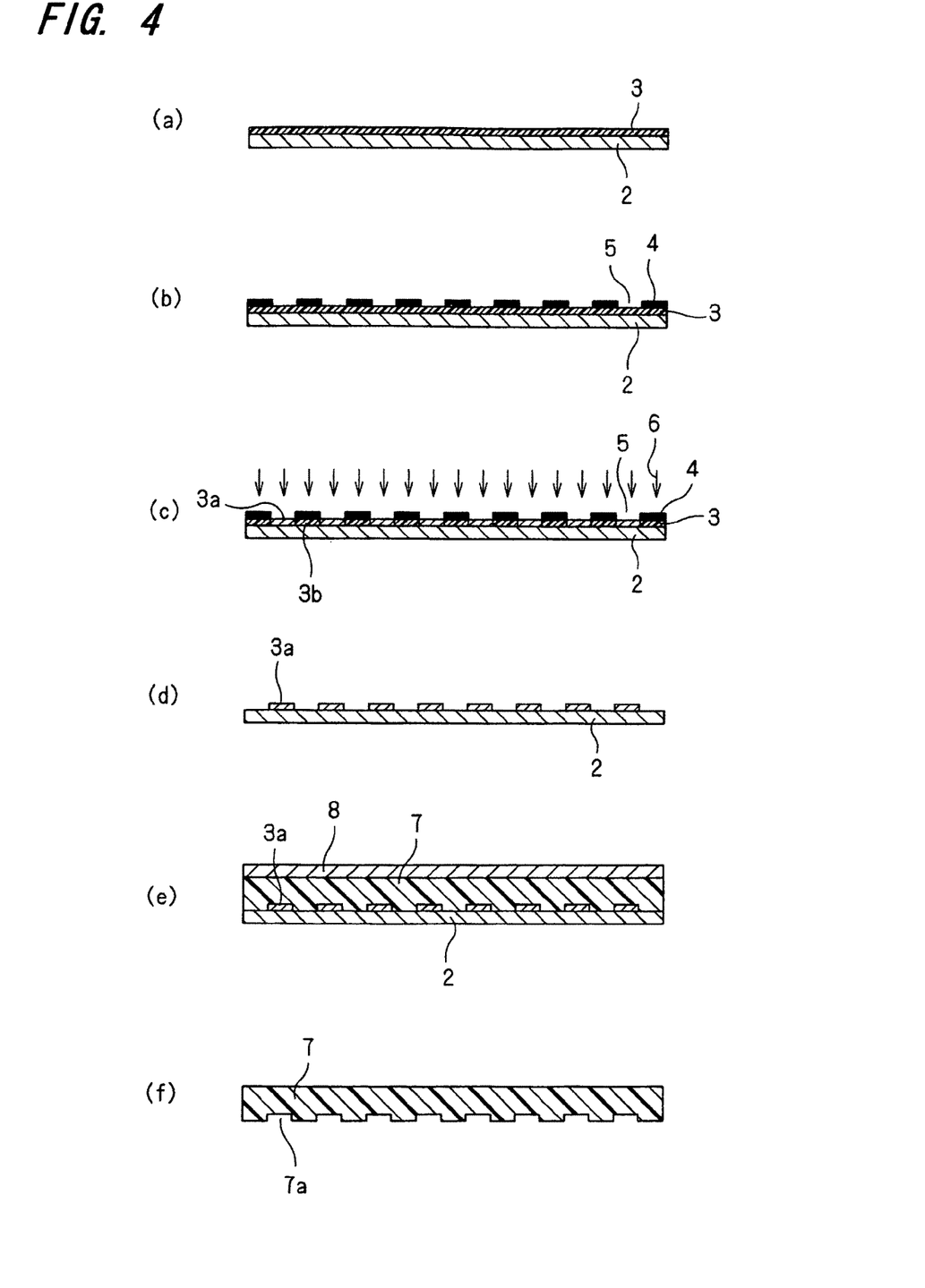
FIG. 4 is an explanatory view of a production process of a substrate (Embodiment 1)

As shown in FIG. 4(a), SU-8-2 (manufactured by MicroChem Corp.) is spin-coated as a negative resist 3 on a glass substrate 2, and semi-cured by heating it in an oven.

Then, a photoresist is applied on the semi-cured negative resist 3, which is then exposed and developed to form a mask 4 having an opening 5 as shown in FIG. 4(b). The patterns of grooves 22 and 24; 32 and 34 which become the channels are formed in the mask 4 as well as those of columnar structures 28 and 38 are also formed in the grooves 22 and 24; 32 and 34 near the branch starting position 12 (see FIG. 1).

Then, as shown by arrows 6 in FIG. 4(c), the ultra violet light is exposed to the negative resist 3 through the opening 5 of the mask 4, and then the negative resist 3 is heated again in the oven. Thereby, only a portion 3a facing the opening 5 of the mask 4 is finally cured in the negative resist 3.

Then, the negative resist 3 is developed by a developer specific for SU-8 and washed with water to remove an unnecessary portion 3b of the negative resist. Then, by drying, the template where the portion 3a which becomes the channel has been formed on the glass substrate 2 is completed.

(2) Production of Channel

A barrier coat (mold releasing agent) is spin-coated on the completed template. Then, as shown in FIG. 4(e), the circumference of the glass substrate 2 on which a convex pattern 3a of the channel has been formed on the upper surface is surrounded with a spacer (not shown in the figure), and PDMS (polydimethylsiloxane) resin 7 is poured therein and cured by heating in the oven.

Then, after cooling, the cured PDMS resin 7 is peeled to complete the substrates 20 and 30 made from PDMS where the channel pattern has been formed on one principal surface (see FIG. 2).

(3) Joining of Substrates

The sides on which the channel pattern has been formed face each other, a polyimide film having a thickness of 7 μm as the thin plate 40 is disposed between the substrates 20 and 30, and the substrates 20 and 30 are closely adhered with each other. Since PDMS has adhesiveness, the thin plate 40 is sandwiched with the substrates 20 and 30 and joined. The portion of the thin plate 40 which traverses the grooves 22 and 32 is sandwiched and supported between the columnar structures 28 and 38. The portion of the thin plate 40 which is exposed in the grooves 24 and 34 is fixed by also providing the columnar structures 28 and 38 in the grooves 24 and 34 and pressing the thin plate 40 to the other substrates 20 and 30 with the tips of the columnar structures 28 and 38.

In the microchip 10 made in this way, since the polyimide film as the thin plate 40 is very thin, even an edge portion of the polyimide film is sufficiently adhered to PDMS of the upper and lower substrates 20 and 30, and leaking of blood samples never posed a problem particularly even without sealing.

Moreover, PDMS is originally hydrophobic, and the blood cannot be directly poured in by the capillary phenomenon. Thus, it is necessary that the inner surface of the channels 11, 13 and 14 is hydrophilized by some method. Thus, the substrates 20 and 30 are produced using PDMS to which a hydrophilizing agent has been added.

Instead of adding the hydrophilizing agent, the inner surface may be hydrophilized by oxygen plasma. For example, using a reactive ion etching apparatus, the inner surface of the channels in the substrates is hydrophilized by the oxygen plasma. The hydrophilization is performed by substituting a methyl group on the surface of PDMS with a hydroxyl group by the oxygen plasma.

Even if the hydrophilization is given, if the contact angle with respect to the blood sample is less than 70 degrees, then the blood flows only in the corner portion of the channels 11, 13 and 14 having the rectangular cross section due to the capillary phenomenon. Thus, uniform flow is not made in the cross section. If the contact angle with respect to the blood sample is 70 degrees or more, when the blood sample runs in the channels 11, 13 and 14 by the capillary phenomenon, uniform flow is made in the cross section.

Therefore, it is preferable that the hydrophilization is performed so as to assure the contact angle of 70 degrees or more with respect to the blood sample in at least the inner surface of the separation channel 11 and the blood cells are made to settle out in the uniform flow state in the cross section.

In the microchip 10 made in the above way, the substrates 20 and 30 are transparent and the thin plate 40 is translucent. Thus, the state inside the microchip 10 can be observed from the outside. Therefore, the reaction in the channel can be detected optically, and the microchip is suitable for blood examinations.

Embodiment 2

A microchip 100 for blood examinations (herein after also referred to as the "microchip" simply) in Embodiment 2 will be described with reference to FIG. 5 to FIG. 8.

Figure 5:
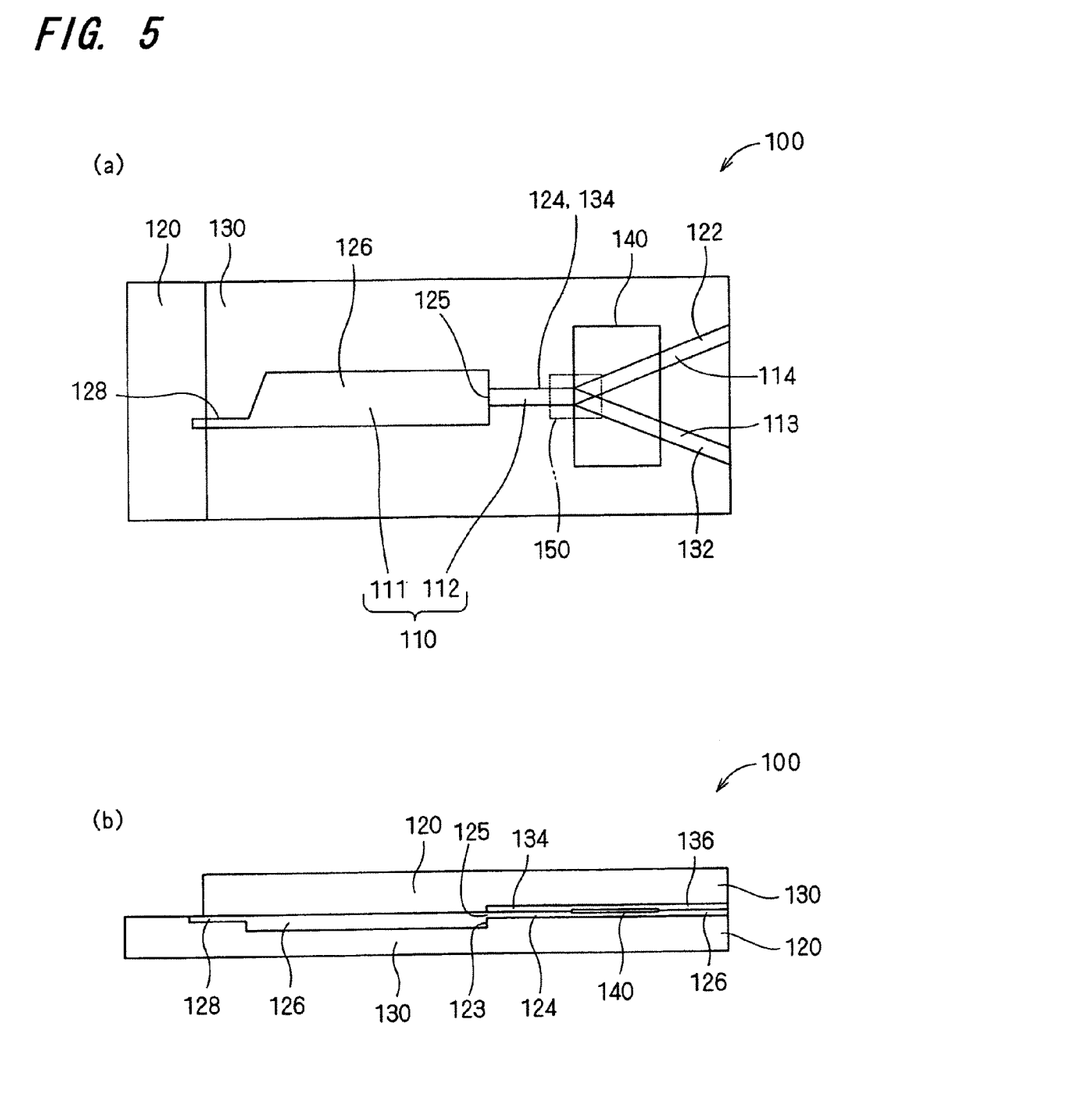
FIG. 5 is (a) a plane transparent view and (b) a side transparent view of a microchip for blood examinations (Embodiment 2)
Figure 6:
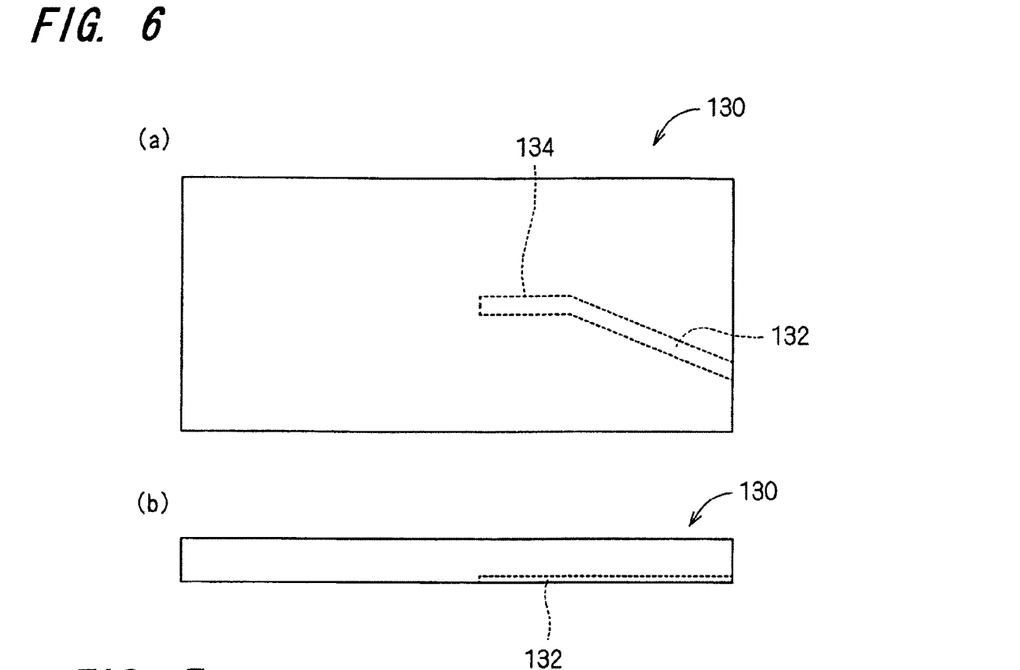
FIG. 6 is (a) a plane view and (b) a side view of an upper side substrate (Embodiment 2)
Figure 7:
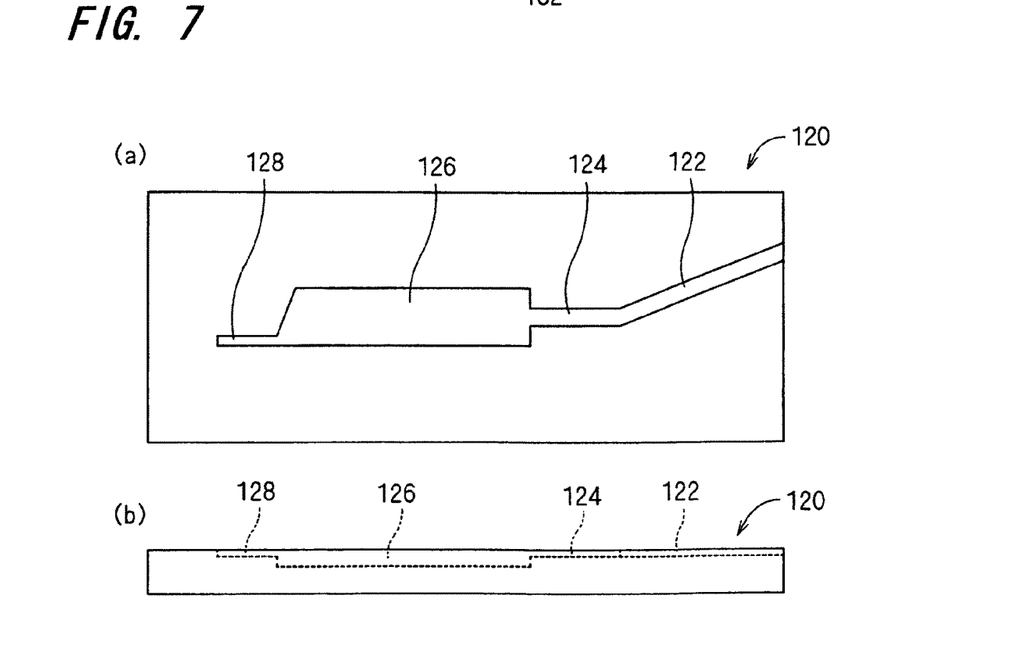
FIG. 7 is (a) a plane view and (b) a side view of a lower side substrate (Embodiment 2)

The microchip 100 in Embodiment 2 is constituted in almost the same way as the microchip 10 in Embodiment 1. FIG. 5 is (a) a plane transparent view and (b) a side transparent view of the microchip 100. FIG. 6 is (a) a plane view and (b) a side view of an upper substrate 130. FIG. 7 is (a) a plane view and (b) a side view of a lower substrate 120.

As shown in FIG. 5 to FIG. 7, in the microchip 100, a thin plate 140 for forming the separator structure is held between substrates 120 and 130 where grooves 122 and 124; 132 and 134 which become Y-shaped channels have been formed, and a separation channel 110 is branched into a first branch channel 113 and a second branch channel 114, as is the case with Embodiment 1.

Differently from Embodiment 1, the groove 134 which becomes the separation channel 110 is formed only partway on the upper substrate 130.

Also, the first groove 124 and the second groove 126 which are different in width and depth as the grooves which become the separation channel 110 are formed on the lower substrate 120. One end of the first groove 124 is connected with the groove 122 which becomes the second branch channel 114, and the other end is connected with the second groove 126. The second groove 126 is relatively wider and deeper than the first groove 124, and a step 123 is formed on its bottom surface.

The groove 134 in the upper substrate 130 is overlapped on the first groove 124, and a downstream side channel 112 of the separation channel 110 is formed by the groove 124 in the lower substrate 120 and the groove 134 in the upper substrate 130.

The portion where no groove is formed in the upper substrate 130 is overlapped on the second groove 126, and an upstream side channel 111 of the separation channel 110 is formed by the second groove 126 alone. The upstream side channel 111 and the downstream side channel 112 of the separation channel 110 are connected via an opening 125 alone which communicates between the first groove 124 and the second groove 126.

A groove 128 connected with the second groove 126 is formed in the lower substrate 120. The portion where no groove is formed in the upper substrate 130 is overlapped partway on this groove 128, the side of the groove 128 opposite to the second groove 166 is exposed, and an opening for supplying the blood sample from the outside is formed there.

In this way, a) the channel is narrowed down to increase a fluid resistance by providing the opening 125 reducing a cross sectional area in a midpoint of the separation channel 110 and b) the flow rate of the blood sample drawn in by the capillary phenomenon is slowed down by thickening the upstream side channel 111 of the separation channel 110, thereby obtaining reliably the period of time for settling out the blood cells.

Also, the blood cells are hooked into the step 123 provided between the upstream side channel 111 and the downstream side channel 112 in the separation channel 110. Thus, it is possible to reduce the rate of the blood cells in the blood sample which flows to the downstream side channel 112 of the separation channel 110 until the lower side of the upstream side channel 111 of the separation channel 110 is filled with the blood cells.

As a result, the microchip 100 of the present Embodiment 2 can more accurately separate the blood plasma.

Figure 8:
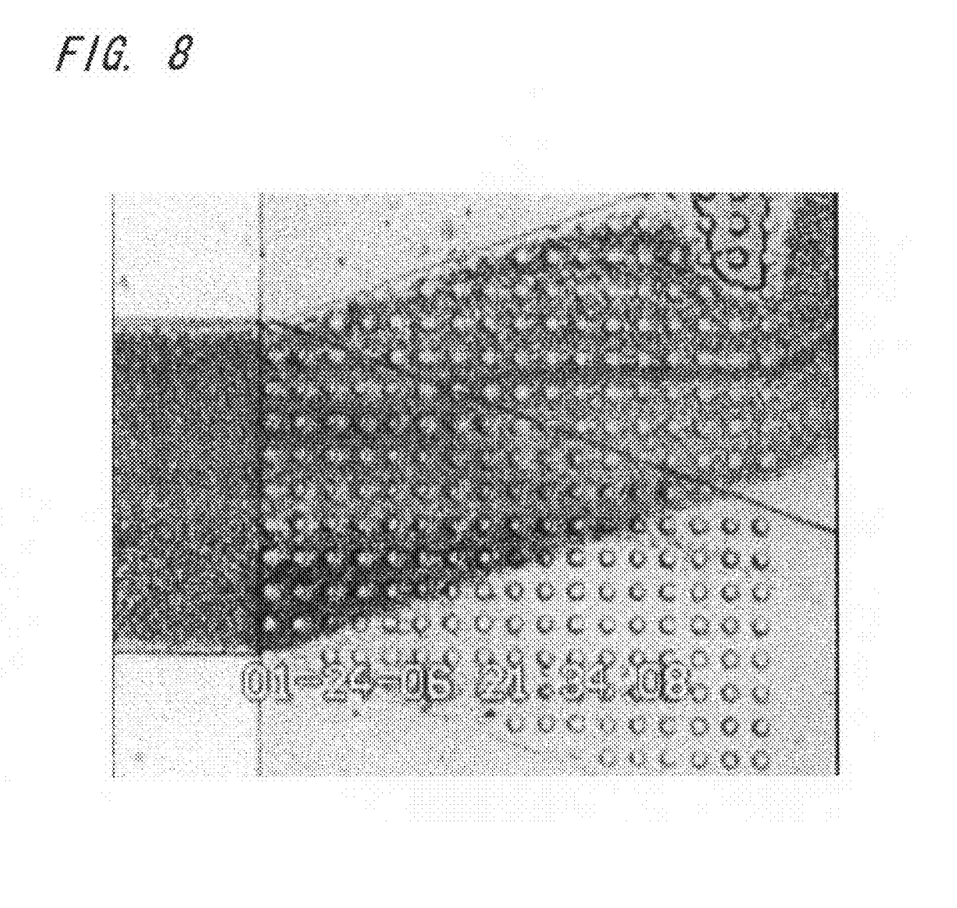
FIG. 8 is a magnified photograph around the channel bifurcation (Embodiment 2)

FIG. 8 is one example of photographs which magnified a vicinity of a region 150 (see FIG. 5) near the branch starting position of the microchip 100 produced in the same way as the example of production in Embodiment 1. The left side of the figure shows the separation channel 110, an upper right channel in the figure is the second branch channel 114 in which the blood cells are flown and a lower right channel in the figure is the first branch channel 113 in which the blood plasma is flown. The blood cells have a dark color and the blood plasma is transparent. It has been shown that the blood cells are flown out only in the upper right second branch channel 114 in the figure and only the blood plasma is acquired from the lower right first branch channel 113 in the figure. At this time, 99% or more of the blood cells could be separated from the blood sample which was flown at a flow rate of 100 μm/second.

In the microchip in this photograph, the width of the downstream side channel 112 of the separation channel 110 and the branch channels 113 and 114 (corresponding to $W_0$, $W_1$ and $W_2$ in the FIG. 1) is 1,000 μm, the depth of the downstream side channel 112 of the separation channel 110 is 100 μm and the depth of both branch channels 113 and 114 is 50 μm. The width of the first groove 124 which forms the upstream side channel 111 of the separation channel 110 is 2,500 μm, the depth thereof is 150 μm, the width of the second groove 124 which forms the lower part of the downstream side channel 112 of the separation channel 110 is 1,000 μm and the depth thereof is 50 μm.

Near the branch starting position, many columnar structures having a diameter of 50 μm are formed with intervals of 100 μm to hold the thin plate 40 in order to prevent a deflection of the separator structure. A space of 50 μm which is larger than the diameter of the blood cells (approximately 8 μm) is provided between adjacent columnar structures.

The thickness of the thin plate is 7 μm, and there was no leakage of the blood cells from the space between the substrates 120 and 130.

Embodiment 3

Figure 9:
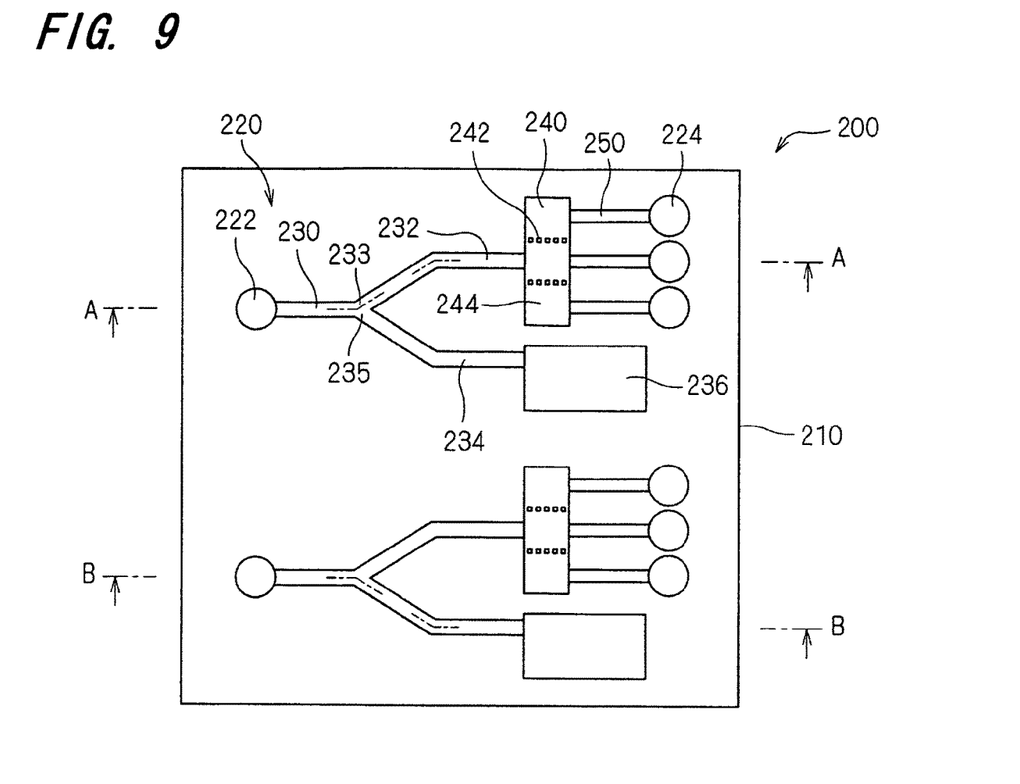
FIG. 9 is a plane transparent view of a microchip array for blood examinations (Embodiment 3)
Figure 10:
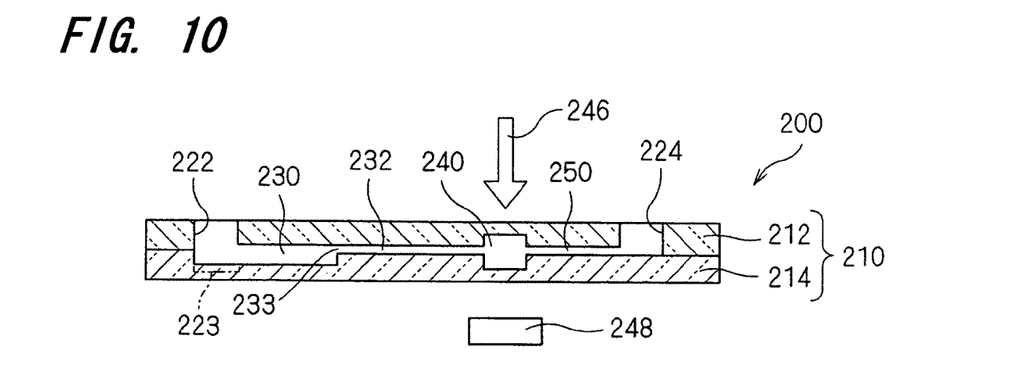
FIG. 10 is a cross sectional view cut along a line of A-A in FIG. 9 (Embodiment 3)
Figure 11:
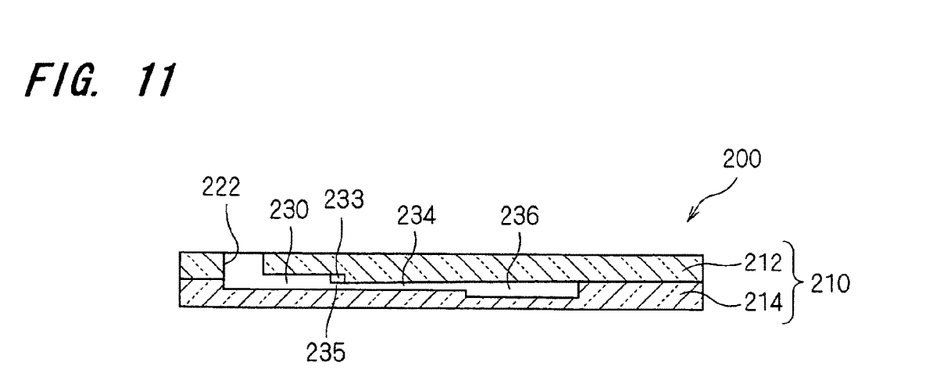
FIG. 11 is a cross sectional view cut along a line of B-B in FIG. 9 (Embodiment 3)

A microchip array 200 for blood examinations (herein after also referred to as the "microchip array" simply) of Embodiment 3 will be described with reference to FIG. 9 to FIG. 11. FIG. 9 is a plane transparent view of the microchip array 200. FIG. 10 is a cross sectional view cut along the line A-A in FIG. 9. FIG. 11 is a cross sectional view cut along the line B-B in FIG. 9.

The microchip array 200 of Embodiment 3 is constituted similar to Embodiment 1 and Embodiment 2. Different points from Embodiment 1 and Embodiment 2 will be described mainly below.

As shown in FIG. 9 to FIG. 11, in the microchip array 200, two pairs of channel structures 220 are formed on a substrate body 210 obtained by joining substrates 212 and 214 together having a pair of planes which are mutually parallel. For example, glass substrates are used for the substrates 212 and 214, and the channel structure 220 is formed by plasma etching or ion beam etching using fluorine based gas such as $CH_3F$.

The channel structure 220 includes a main channel 230 and two branch channels 232 and 234. As is the case with Embodiment 2, the main channel 230 is formed by the grooves provided in the surfaces to be joined in respective substrates 212 and 214 (i.e., the interface between the joined substrates 212 and 214) so as to be mutually facing. The branch channels 232 and 234 are formed between the groove provided in the surface to be joined in one substrate 212 or 214 and the portion where no groove is formed in the other substrate 214 or 212, and are mutually separated. In the surfaces to be joined in the respective substrates 212 and 214, the groove which forms the main channel 230 and the grooves which form the branch channels 232 and 234 are connected and communicated at their one ends, and communication ports 233 and 235 are formed in the portion to be connected with their one ends.

In the figures, a blood introduction inlet 222 which is communicated with the other end of the main channel 230 is formed in the upper one substrate 212.

The other end of one branch channel 232 is communicated with a blood plasma bath 240, and the other end of the other branch channel 234 is communicated with a blood cell pool 236.

The blood plasma bath 240 is formed by concave portions provided facing the surface to be joined in the respective substrates 212 and 214 as shown in FIG. 10. The blood plasma bath 240 is partitioned by partitions 242 into multiple examination regions 244 as schematically shown in FIG. 9. The partition 242 may be constituted to be inserted in the blood plasma bath 240 or may be constituted to be previously disposed in the blood plasma bath 240 and be opened/closed. A reagent solution is supplied to each examination region 244 partitioned by the partition 242, via a reagent solution inlet 224 and a reagent channel 250 formed on the upper one substrate 212 in the figure.

When the blood sample is examined using the microchip array 200, the microchip array 200 is disposed in a substantially horizontal direction and the blood sample is supplied to the blood introduction inlet 222 of each channel structure 220. As the supplied blood sample is flown in the laminar flow state in the main channel 230, the blood cells in the blood sample settle out to separate the blood plasma and the blood cells in up and down directions. And, in one end of the main channel 230, the blood cells are flown in the lower side branch channel 234 and introduced into the blood cell pool 236 in the figure. Meanwhile, the majority of the blood plasma is flown in the upper side branch channel 232 and introduced into the blood plasma bath 240 in the figure. When the blood plasma is pooled in the blood plasma bath 240, the blood plasma bath 240 is partitioned by the partitions 242 into multiple examination regions 244. Then, the reagent solution is supplied to each partitioned examination region 244 from the reagent solution inlet 224 via the reagent channel 250, and a reaction with the reagent is examined.

For example, the microchip array 200 is loaded in a blood examination apparatus, laser light is irradiated from blood examinations apparatus to the blood plasma bath 240 as shown by the arrow 246, the transmitted light through the blood plasma bath 240 is measured by a light sensor 248 in blood examinations apparatus, and the reaction with the reagent is examined based on the change in the transmitted light. At this time, one laser light may be scanned for respective examination regions 244 in the blood bath 240, or each distinct laser light may be irradiated to each examination region 244. Instead of measuring the transmitted light, the examination may be constructed to measure a reflected light from the blood plasma bath 240.

In order to transmit sufficient light for the examination, the substrates 212 and 214 may be thinned or may be provided with a hole or a window as necessary. The blood sample may be examined by the method other than the above. For example, an electric property may be measured.

As shown by a virtual line in FIG. 10, if a bottom surface 223 of the blood introduction inlet 222 is constituted to become lower than the main channel 230, it becomes difficult for the blood cells settling out near the bottom surface 223 of the blood introduction inlet 222 to enter the main channel 230 when the blood sample is supplied from the blood introduction inlet 222. Thus, a separation accuracy of the blood plasma can be enhanced because a supernatant portion of the blood sample, in which the amount of blood cells has been decreased, enters the main channel 230.

In order to uniformly flow to settle out the blood cells in the main channel 230, an inner surface of the main channel 230 is constituted to have the contact angle of 70 degrees or more with respect to the blood by giving a surface treatment thereto as necessary. The depth of the main channel 230 (dimension of the substrates 232 and 234 in the direction perpendicular to the interface) is 1 mm or less so that the flow keeps the laminar flow state in the main channel 230. The sides of the branch channels 232 and 234 of the main channel 230 may be provided with the separator structure as is the case with Embodiment 1 and Embodiment 2.

When the microchip array 200 of Embodiment 3 is used, several types of blood examinations can be performed collectively at one time.

SUMMARY

As described above, using the microchip for blood examinations and the microchip array for blood examinations, the blood plasma can be conveniently separated on the microchip.

The present invention is not limited to the embodiments described above, and can be carried out by adding various modifications.

For example, in order to make the channel in the substrate body, three or more substrates may be used. When the substrate body is made by joining two substrates, the channels may be formed only in one substrate. It is also possible to constitute the substrate body with one substrate alone. As the substrate body, the platy ones obtained by joining the substrates having a pair of planes which are mutually parallel were exemplified, but the substrate body is not limited thereto, and may have any shape.

The invention claimed is:

1. A microchannel for separating blood plasma comprising:
    a substrate body;
    a separation channel which is formed inside the substrate body and extended in parallel to a longitudinal direction of the substrate body from a first end to a second end opposite said first end;
    at least two, first and second communication ports, which are formed at said first end of the separation channel;
    first and second branch channels, which are formed inside the substrate body and communicate with the first and second communication ports, respectively; and
    a separator structure, which divides the separation channel horizontally said first end of the separation channel and which is extended from a position where the first and second branch channels start to branch to a middle position of the separation channel between said first end and said second end;
    wherein in a state where the substrate body is extended perpendicularly to a direction of gravitational force, a blood sample containing blood cells and plasma flows from said second end of the separation channel to said first end of the separation channel, the blood cells in the blood sample settle out before the blood sample reaches said first end of the separation channel; and
    wherein the blood cells, having settled out, are introduced into one branch channel located at a lower side of the direction of gravitational force among the first and second branch channels and a majority of the plasma is introduced into the other branch channel located at a higher side of the direction of gravitational force.

2. The microchannel for separating the blood plasma according to claim 1, wherein the substrate body comprises first and second substrates mutually joined,
    wherein a first portion of the separation channel is formed in the first substrate and a second portion of the separation channel is formed in the second substrate, and
    wherein the separator structure is constituted by a sheet-like member held between the first and second substrates so as to traverse said first end of the separation channel.

3. The microchannel for separating the blood plasma according to claim 1, wherein an inner surface of the separation channel has a contact angle of 70 degrees or more with respect to the blood sample.

4. The microchannel for separating the blood plasma according to claim 1, wherein a depth line normal to the direction of flow in the separation channel is 1 mm or less.

5. The microchannel for separating the blood plasma according to claim 1, wherein the separator structure is a thin plate, having a tip which is located upstream of the first and second branch channels, the thin plate extending to the middle position of the separation channel.

6. A microchannel for separating blood plasma comprising:
    a substrate body containing a first substrate having first and second planes which are mutually parallel and a second substrate having third and fourth planes which are mutually parallel, wherein the second plane in the first substrate and the third plane in the second substrate are joined;
    a main channel formed by disposing a first groove formed in the second plane of the first substrate and a second groove formed in the third plane of the second substrate, the grooves mutually facing each other and extending along the interface between the second plane of the first substrate and the third plane of the second substrate, said main channel extending from a first end to a second end opposite said first end;

first and second communication ports formed respectively in the first groove of the first substrate and the second groove of the second substrate in said first end of the main channel;

first and second branch channels formed in the second plane of the first substrate and in the third plane of the second substrate, respectively, communicating with the first communication port and the second communication port, respectively, and extending along the interface to be mutually separate; and a separator structure which divides the main channel horizontally from said first end where the branch channels start to branch to a middle position of the main channel between said first end and said second end of the main channel;

wherein the main channel has a structure where a blood sample including blood cells and plasma flows as a laminar flow state from the other said second end to said first end of the main channel in a state where the interface is disposed to extend perpendicularly to a direction of gravitational force, and wherein the blood cells in the blood sample settle out in a lower side of a direction of gravitational force before the blood sample reaches said first end of the main channel, the blood cells are introduced into the first branch channel located at the lower side of the direction of gravitational force and a majority of the plasma is introduced into the second branch channel located at a higher side of the direction of gravitational force.

7. The microchannel for separating the blood plasma according to claim 6, wherein the separator structure is formed of a sheet-like member held between the first and second substrates so as to traverse the first end of the main channel.

8. The microchannel for separating the blood plasma according to claim 7, wherein first and second columnar structures extending in the direction perpendicular to the interface are formed respectively in the first and second grooves of the main channel formed in the first and second substrates, and wherein the sheet-like member which forms the separator structure is held between the first columnar structure and the second columnar structure.

9. The microchannel for separating the blood plasma according to claim 6, wherein the separator structure is a thin plate, having a tip which is located upstream of the first and second branch channels, the thin plate extending to the middle position of the separation channel.

10. A microchannel for separating blood plasma comprising:

a substrate body;

a separation channel which is formed inside the substrate body and extended in parallel to a longitudinal direction of the substrate body from a first end to a second end opposite said first end;

at least two, first and second communication ports which are formed at said first end of the separation channel; and first and second branch channels which are formed inside the substrate body and communicate with the first and second communication ports, respectively;

wherein in a state where the substrate body is extended perpendicularly to a direction of gravitational force, a blood sample containing blood cells and plasma-flows from said second end to said first end of the separation channel, the blood cells in the blood sample settle out before the blood sample reaches said first end of the separation channel, wherein the blood cells, having settled out, are introduced into the first branch channel located at a lower side of the direction of gravitational and a majority of the plasma is introduced into the second branch channel located at a higher side of the direction of gravitational, a separator structure which projects from said first end to a middle position of the separation channel between said first end and said second end of the separation channel and divides said first end of the separation channel into two portions in the thickness direction;

wherein the two portions divided by the separator structure are in fluid communication with the first and second communication ports, wherein the substrate body comprises first and second substrates mutually joined, wherein a first portion of the separation channel is formed in the first substrate and a second portion of the separation channel is formed in the second substrate, wherein the separator structure is constituted by a sheet-like member held between the first and second substrates so as to traverse said first end of the separation channel, and wherein first and second columnar structures extending in the thickness direction are formed respectively in the first and second portions of the separation channel formed in the first and second substrates; and wherein the sheet-like member which forms the separator structure is held between the first columnar structure and the second columnar structure.

* * * * *